United States Patent [19]

Nagatomi et al.

[11] Patent Number: 5,883,260

[45] Date of Patent: Mar. 16, 1999

[54] PROCESS FOR PRODUCING 1-SUBSTITUTED-HYDANTOINS

[75] Inventors: Toshio Nagatomi, Toyonaka; Shigeki Yokoi, Misawa; Yoshimi Yamada, Osaka, all of Japan

[73] Assignee: Sumitomo Chemical Company, Limited, Osaka, Japan

[21] Appl. No.: 880,502

[22] Filed: Jun. 23, 1997

[51] Int. Cl.⁶ ................................................... C07D 233/40

[52] U.S. Cl. .................. 548/314.1; 548/162; 548/301.4; 548/317.1; 558/313

[58] Field of Search ................. 548/314.1, 162, 548/301.4, 317.1; 558/313

[56] References Cited

U.S. PATENT DOCUMENTS 3,946,033  3/1976  Iwata et al. ........................... 260/309.5

Primary Examiner—Johann Richter
Assistant Examiner—Ebenezer Sackey
Attorney, Agent, or Firm—Pillsbury Madison & Sutro LLP

[57] ABSTRACT

The subject is to provides a process for producing 1-substituted-hydantoins of Formula I:

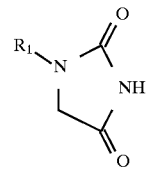

wherein $R_1$ represents d hydrocarbon group which may be substituted and others,
cheracterized by reacting N-sustituted-N-alkcycarbonylamnilo-acetonitrile of Formula II:

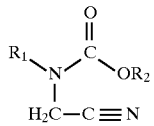

wherein $R_2$ represents an alkyl group and others,
with an alkali metal hydroxides or the like and then treating with an acid.

11 Claims, No Drawings

PROCESS FOR PRODUCING 1-SUBSTITUTED-HYDANTOINS

FIELD OF THE INVENTION

The present invention relates to a process for producing 1-substituted-hydantoins.

BACKGROUND OF THE INVENTION

1-Substituted-hydantoins have been known as useful intermediated for producing agricultural chemicals and pharmaceuticals (for example, U.S. Pat. No. 4,176,189 and U.S. Pat. No. 5,308,853 and others).

A further method for producing the 1-substituted-hydantoins has been desired.

SUMMARY OF THE INVENTION

The present inventors have found that 1-substituted-hydantoins of Formula I shown below can be readily produced by reacting N-substituted-N-alkoxycarbonylamino-acetonitrile of Formula II shown below with hydroxide and also found a process for producing N-substituted-N-alkoxycarbonylamino-acetonitrile, whereby completing the invention.

The present invention provides:

1. a process for producing 1-substituted-hydantoin of Formula I:

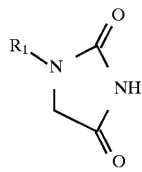

wherein $R_1$ represents a hydrocarbon group which may be substituted or a heterocyclic group which may be sutbstituted, which comprises the steps of:
(a) reacting N-substituted-N-alkoxycarbonylamino-acetonitrile of Formula II:

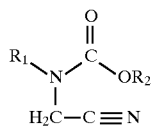

wherein $R_1$ is the same an defined above and $R_2$ represents an alkyl group or a benzyl group which may be subtituted, with hydroxide selected from an alkali metal hydroxide and an alkaline earth metal hydroxide and then,
(b) treating the resultiny with an acid; and 2. a process for pruducing N-substituted-N-alkoxycarbonylaminoacetonitrile of Formula II:

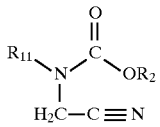

wherein $R_{11}$ represents a primary or secondary hydrocarbon group which may be substituted and $R_2$ represents an alkyl group or a benzyl group which may be substituted, which comprises reacting N-alkoxycarbonylamino-acetonitrile of Formula III:

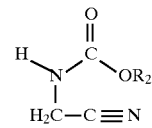

wherein $R_2$ represents the same as defined above, with a compound of Formula IV:

wherein $R_{11}$ is the same as defined above and x represents a halogen atom or a group of the Formula:

wherein Y represents an alkyl group or a phenyl group which may be substituted, in the presence of a base; and 3. N-alkynyl-N-alkoxycarbonylamino-acetonitrile of Formula V:

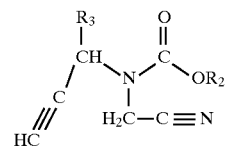

wherein $R_2$ represents an alkyl group or a benzyl group which may be substituted and $R_3$ represents a hydrogen atom or an alkyl group.

DESCRIPTION OF PREFERRED EMBODIMENTS

Description will be made to the process for producing 1-substituted-hydantoin of Formula I as defined above, which comprises the steps of:
(a) reacting N-substituted-N-alkoxycarbonylamino-acetonitrile of Formula II as defined above with hydroxide selected from an alkali metal and an alkaline earth metal hydroxide and then,
(b) treating the resulting with an acid.

The hydrocarbon group which may be substituted or a heterocyclic group which may be substituted for $R_1$ is not particularly limited insofar as the substituent group does not adversely affect the reaction steps (a) and (b).

The hydrocarborn group which may be substituted includes, for example, an alkyl group (C1–C8 alkyl group such as methyl, ethyl, propyl, isopropyl, butyl, sec-butyl or the like), an alkenyl group (C3–C8 alkenyl group such as 2-propenyl, 2-methyl-2-propenyl, 2-butenyl, 1-methyl-2-propenyl, 2-nethyl-2-propenyl or the like), a halogenated alkenyl group (C3–C8 halogenated alkenyl group such as 2-chloro-2-propenyl, 3-chloro-2-propenyl, 3,3-dichloro-2-propenyl, 2-methyl-2-propenyl or the like), an alkynyl group (C3–C8 alkynyl groups such as 2-propynyl, 1-methyl-2-propynyl or the like), a benzyl group which may be substituted [C7–C12 benzyl which may be substituted such as phenylnethyl, (p-methylphenyl)methyl, (p-chlorophenyl)methyl, (p-methoxyphenyl)methyl or the like], a phenyl group which may be substituted (phenyl, p-methylphenyl, p-chlorophenyl, p-methoxyphenyl or the like.

The heterocyclic group which may be substituted includes a pyridyl group which may be substituted, for example, 2-pyridyl, 3-pyridyl, 4-methyl-2-pyridyl or the like.

The alkyl group for $R_2$ includes a C1–C8 alkyl group such as methyl, ethyl, propyl, isopropyl, butyl. sec-butyl and the like.

The benzyl group which may be substituted for $R_2$ includes C7–C12 benzyl which may be substituted such as phenylmethyl, (p-methylphenyl)methyl, (p-chlorophenyl) methyl, (p-methoxyphenyl)methyl and the like.

Exmples of the compounds of Formula II include:

N-(2-propynyl)-N-methoxycarbonylamino acetonitrile,

N-(2-propynyl)-N-ethoxycarbonylamino acetonitrile,

N-(2-propyayl)-N-benzyloxycarbonylamino acetonitrile,

N-butyl-N-methoxycarbonylamino acetonitrile,

N-(2-propenyl)-N-methoxycarbonylamino acetonitrile,

N-(2-propenyl)-N-ethoxycarbonylamino acetonitrile,

N-(2-chloro-2-propenyl-N-methoxycarbonylamino acetonitrile,

N-(2-chloro-2-propenyl)-N-ethoxycarbonylamino acetontrile,

N-benzyl-N-metboxycarbonylamino acetonitrile,

N-phenyl-N-methoxycarbonylamino acetonitrile and

N-(2-pyridyl)-methoxycarbonylamino acetonitrile.

Among these compound, the compound of Formula V wherein $R_3$ is an alkyl group or a hydrogen atom is a novel compound.

The alkyl group for $R_3$ includes C1–C4 alkyl groups such as methyl, ethyl and the like.

Examples of the Compound of Formula V includes:

N-(2-propynyl)-N-methoxycarbonylamino acetonitrile,

N-(2-propynyl)-N-ethoxycarbonylamino acetonitrile,

N-(2-propynyl)-N-benzyloxycarbonylamino acetonitrile,

N-(1-methyl-2-propynyl)-N-methoxycarbonylamino acetonitrile and

N-(1-methyl-2-propynyl)-N-ethoxycarbonylamino acetonitrile.

N-Substituted-N-alkoxycarbonylamino-acetonitrile of Formula II can be produced by reacting N-substituted amino-acetonitrile of Formula IV:

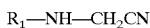

$R_1$—NH—$CH_2CN$ wherein $R_1$ is as defined above,
with chlorcforte of Formula VII:

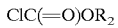

ClC(=O)O$R_2$ wherein $R_2$ is as defined above,
in the presence of a hydrogen chloride acceptor (for details, see, for example, JP-A-50-105829).

N-Substituted amino-acetonitrile of Formula IV used above can be produced, for example, by Strecker synthesis in which an amine of Formula: $R_1$—$NH_2$, wherein $R_1$ is as defined above, is reacted with formaldehyde and HCN (or KCN or NaCN) [for details, see J. Am. Chem. Soc., 2865, (1959); Justus Liebig's Annalen, 639, 102, (1961)].

The hydroxide to be used in step(a) is selected from an alkali metal hydroxide and an alkaline earth metal hydroxide.

The alkali metal hydroxide includes sodium hydroxide, potassium hydroxide and the like and the alkaline earth metal hydroxide includes barium hydroxide, calcium hydroxide and the like.

The amounts of said alkali metal hydroxide and alkaline earth metal hydroxide are usually 0.8 to 1.5 moles and 0.4 to 0.75 mole, respectively, based on 1 mole of N-substituted-N-alkoxyrarbonylamino-acetonitrile of Formula II.

The reaction is usually conducted in an inert solvent and such solvent includes for example, water, an alcohol such as t-butanol or the like, an ether such as tetrahydrofuran, 1,4-dioxane, 1,2-dimethoxyethane or the like, an aromatic hydrocarbon such as benzene, toluene, chlorobenzene or the like, dimethylsulfoxide, N,N-dimethylformamide or the like, or a mixture thereto.

The reaction temperature is usually −10° to 80° C. The reaction solution after completion of the reaction may be used as such in the following step (b).

In step(b), the acid to be used includes hydrogen chloride gas, hydxrochloric acid, sulfuric acid or the like and the amount of said acid is an amount sufficient for neutralizing the solution or usually about 1 mole based on 1 mole of the alkali metal hydroxide used in the step(a).

The reaction temperature is usually −10° to 80° C.

The reaction solution after completion or the reaction may be, for example, concentrated and the residue may be extracted using a solvent such as alcohols including methanol, ethanol and the like, acetonitrile, acetone or the like, filtered to remove inorganic salts and concentrated, or alternatively, concentrated and the residue may be recrystallized directly from water or the like to isolate the desired 1-substituted-hydantoin of Formula I, which can be further purified, it necessary, by recrystallization or various chromatographies.

Examples of the hydantoins of Formula I thus obtained include:

1-butylhydantoin, 1-(2-propynyl)hydantoin, 1-(1-methyl-2-propynyl)hydantoin, 1-(2-propenyl)hydantoin, 1-(2-chloro-2-propenyl)hydantoin, 1-(3-chloro-2-propenyl)hydantoin and 1-benzylhydantoin.

Other specific examples of the compounds of Formula I include:

1-phenylhydantoin, and 1-(2-pyridyl)hydantoin.

Next, description will be made to the process for producing N-substituted-N-alkoxycarbonylamino-acetonitrile of Formula II as defined above, which comprises reacting N-alkoxycarbonylamino-acetonitrile of Formula III as defined above with a compound of Formula IV as defined above in the presence of a base.

For $R_{11}$ in Formula IV the primary or secondary hydrocarbon group which may be substituted is not particularly limited insofar as the group does not adversely affect the reaction.

The primary or secondary hyocarbon group which may be substituted includes;

a primary or secondary alkyl group (a C1–C8 primary or secondary alkyl group such as methyl, ethyl, propyl, isopropyl, butyl, sec-butyl or the like), a primary or secondary alkenyl group (a C3–C8 primary or secondary alkenyl group such as 2-propenyl, 2-methyl-2-propenyl, 2-butenyl, 1-methyl- 2-propenyl, 2-methyl-2-propanyl or the like), a halogenated primary or secondary alkenyl group (a C3–C8 halogenated primary or secondary alkenlyl group such as 2-chloro-2-propenyl, 3-chloro-2-propenyl, 3,3-dichloro-2-propenyl, 2-methyl-2-propenyl or the like), a primary or secondary alkynyl group (C3–C8 primary or secondary alkynyl group such as 2-propynyl, 1-methyl-2-propynyl or the like), and a benzyl group which may be substituted [C7–C12 benzyl which may be substituted such as phenylmethyl, (p-methylphenyl)methyl, (p-chlorophenyl)methyl, (p-methoxyphonyl)methyl or the like].

Specific examples of the compounds of Formula III include:

N-methoxycarbonylamino acetonitrile,

N-ethoxycarbohylamino acetonitrile and

N-benzyloxycarbonylamino acetonitrile

The halogen atom for x in Formula IV includes chlorine atom, bromine atom and iodine atom.

Y in the group $OSO_2Y$ represents an alkyl group or a phenyl group which may be substituated.

The alkyl group for Y includes C1–C5 alkyl group, such as methyl, ethyl, propyl and the like, and the phenyl group which may be substituted includes phenyl, p-methylphenyl, p-chlorophenyl, p-methoxyphenyl and the like, Specific examples of the compounds of Formula IV include:

1-bromobutane, 3-bromo-1-propyne,

3chloro-1-propene, 2,3-dichloro-1-propene, 2-propynyl methanesulfonate, 2-propynyl p-toluenesulfonate, 1-methyl-2-propynyl methanesulfonate and benzyl chloride.

The amount to be used of the compound of Formula IV is usually 1 to 5 moles based on 1 mole of the N-alkoxycarbonylamino-acetonitrile of Formula III.

Alkali metal hydrides such as sodium hydride or the like, alkaline earth metal hydrides such as calcium hydride or the like, alkali metal hydroxides such as sodium hydroxide or the like, alkali metal carbonates such as potassium carbonate or the like, alkali metal alkoxides (for example, C1–C5 alkoxides) such as t-butoxy potassium or the like can be used as the base.

The reaction temperature is usually –30° to 80° C.

The amount of the base is usually 1.0 to 1.5 moles based on the N-alkoxycabonylamino-acetonitrile of Formula II.

The reaction is usually carried out in an inert solvent. such solvent includes alcohols such as t-butanol or the like, others such as tetrahydrofuran, 1,4-dioxane, 1,2-dimethoxyethane or the like, aromatic hydrocarbons such as benzene, toluene, chlorohenzene or the like, dimethylsulfoxide, N,N-dimethylformamide or the like, or a mixture thereof.

In order to improve the reaction velocity and yield, a phase transfer catalyst such as tetrabutyl ammonium bromide, benzyl trimethyl ammonium chloride or the like may be added.

The amount of the phase transfer catalyst is usually 0.05 to 1 mole based on 1 mole of the N-alkoxycarbonylamino-acetonitrile derivative of Formula III.

The reaction solution after completion of the reaction is usually subjected to a post-treatment by combining with water, extracting with an organic solvent immiscible with water such as ethyl acetate, toluene or the like and the extract being concentrated to isolate the desired N-substituted-N-alkoxycarbonylamino-acetonitrile of Formula II.

The isolated product can be further purified, if necessary, by recrystallization or various chromatographies.

The N-alkoxycarbonylamino-acetonitrile of Formula III used above can readily be produced by reacting the chloroformate of formula VII with aminoacetonitrile or its sulfate, hydrogen sulfate or hydrochloride, which are commercially available, in the presence of an acid acceptor. [see: American Chemical Journal, 35, 54, (1906)]. For example N-alkoxycarbonylamino-acetonitrile of Formula III can readily be produced by adding the chloroformate of Formula VII to an aqueous solution of the aminoacetonitrile sulfate, hydrogen sulfate or hydrochloride in the presence of a base as an acid acceptor. (see Production Reference Examples 1 and 2).

The amount of the chloroformate is usually 0.7 to 1.4 mole based on 1 mole of aminoacetonitrile sulfate or hydrochloride.

The aminoacetonitrile sulfate, hydrogen sulfate or hydrochloride is usually dissolved in water and the aqueous solution is adjusted to pH 4 to 9, preferably 4 to 7, by the addition of a base of which amount depends on the kind of the base and usually within a range of 0.01 to 0.5 mole based on 1 mole of the aminoacetonitrile sulfate, hydrogen sulfate or hydrochloride.

Then, the chloroformate of Formula VII is gradually added while controlling the pH of the aqueous solution at 4 to 9, preferably 4 to 7.

The pH can be adjusted by setting a pH meter in the reaction solution and controlled by the addition of a base by manual or automatic means, if necessary.

The base used for controlling pH of the reaction solution includes inorganic base, for example, alkali metal hydroxides such as sodium hydroxide, potassium hydroxide and the like, alkali metal carbonates such as sodium carbonate, potassium carbonate and the like. It is convenient to use the base in the form of an aqueous solution having a concentration of 10% to 50% by weight.

The reaction is usually conducted in an aqueous solvent, and an inert organic solvent such as tetrahydrofuran, acetonitrile or the like can be added to the agueous reaction solution.

The reaction temperature is usually within a range of –5° to 30° C.

After completion of the reaction, the reaction solution is usually subjected to extraction with an organic solvent such as toluene, ethyl acetate or the like and concentrating the extract to isolate the desired N-alkoxycarbonylamino-acetonitrile derivative of Formula III.

In this process, chloroformate having a methy or ethyl group for $R_2$ are preferably used because of the availability of the compounds and good reactivity.

According to the present process the desired compound can be obtained in good satisfactory yield and purity without special purification treating such as distillation.

EXAMPLES

The present invention will now be specifically illustrated by means of Examples, which should not be construed as a limitation upon the scope of the present invention. In Examples, % means % by weight.

In Examples 1 to 10, some of the obtained products were assayed for purity by the area percentage method using gas chlromatography (GC) or by the area percentage method or the internal reference method using liquid chromatography (LC).

The methods for analyses are described below.
Conditions for GC Analysis
Column: TC-70 (manufactured by GL science) of 0.25 mm in diameter and 30 m in length;
Carrier gas: helium, 5 ml/min;
Detector: FID, 250° C.;
Split ratio: 1/10;
Column temperature: raised from 45° C. to 250° C. at 10° C./min and maintained at 250° C. (10 min);
Area percentage method: calculated from the ratio of the peak area of desired product to the total peak area except the solvent peak by dilution solvent.
Conditions for LC Analysis
Column: YMC-Pack C8 A-212 (manufactured by YMC) of 6 mm in diameter and 15 cm in length;
Mobile.phase: a 9:1 mixture of 5 mM aqueous sodium heptanesulfonate/30 mM disodium phosphate and acetonitrile adjusted to pH 3 with phosphoric acid, 1 ml/min, constant composition method;
Detector: UV (200 nm);
Column temperature: 40° C.;
Area percentage method: calculated from the ratio of the peak area of desired product to the total peak area (the analyzing period being twice the clution period for the desired product);
Internal reference method: calculated by measuring the ratio of the detected intensity for the isolated and purified product and that for the internal reference (p-hydxoxy-acetophenone) and measuring the ratio of the peak area of desired product and the reference when measured after adding a predetermined amount of the internal reference to a sample to be analyzed.

In the following Examples, pure yields (%) are calculated based on the parity of the products.
(Examples for Step(a) and Step(b))

Example 1

Into a 100 ml four-necked flask were charged 10.0 g of water and 10.0 g (purity: 98%; 0.064 mole) of N-(2-propynyl)-N-methoxycarbonylamino-acetonitrile and they were heated in a water bath of 40° C. Then, 5.5g (0.066 mole) of 48% aqueous sodium hydroxide solution was added dropwise thereto over 0.1 hour. Subsequently, the mixture was allowed to react in a water bath of 40° C. for 3 hours. As the reaction proceeded, the system changed from 2 phases (upper phase: water; lower phase: N-(2-propynyl)-N-methoxycarbonylamino-acetonitrile) to a homogeneous phase. After the reaction was completed, the mixture was cooled to about 30° C. and neutralized with 7.4 g of 35% aqueous hydrochloric acid, during which crystals precipitated from the solution. The mixture was concentrated to dryness under reduced pressure. The residue was combined with acetonitrile and the mixture was stirred and filtered to remove inorganic salts. The filtrate was treated by a silica gel column to give 6.46 g (purity: 87%; LC internal reference method) a pale yellow solid of 1-(2-propynyl)hydantoin.
Pure yield: 62%
$^1$H-NMR (CDCl$_3$/TMS): δ (ppm): 2.35 (1H, t, J=2.5 Hz), 4.03 (2H, s), 4.21 (2H, d, J=2.5 Hz), 8.7 (1H, br. s) mp: 127° to 129° C.

Example 2

Into a 100 ml four-necked flask were charged 25.2 g of dioxane, 2.66 g of potassium hydroxide (content: 85%; 0.040 mole) and 6.76 g (purity: 90%; 0.037 mole) of N-(2-propynyl)-N-ethoxycarbonylamino-acetonitrile and 19.6 g of water was added dropwise thereto at room temperature. Subsequently, the mixture was allowed to react at room temperature for 20 hours. After the reaction was completed, the mixture was neutralized with 5.4 g of 35% aqueous. hydrochloric acid at room temperature, during which crystals precipitated from the solution. The mixture was concentrated to dryness under reduced pressure. The residue was combined with 10.7 g of water and dissolved by elevating the temperature up to about 60° C. Then, the solution was gradually cooled to 5° C. and precipitated crystals were collected by filtration and washed to give 2.86 g (purity: 90%, LC internal reference method) a pale yellow solid of 1-(2-propycnyl)lydantion.
Pure yield: 51%

Example 3

Into a 100 ml four-necked flask were charged 15.0 g of water and 15.0 g (purity: 90%; 0.072 male) of N-(2-chloro-2-propenyl)-N-methoxycarbonylamino-acetonitrile and they were heated in a water bath of 40° C. Then, 6.7 g (0.080 mole) of 48% aqueous sodium hydroxide isolution was added dropwise thereto over 0.1 hour. Subsequently, the mixture was allowed to react in a water bath of 40° C. for 1.5 hours. As the reaction proceeded, the system changed from 2 phases (upper phase: water; lower phase: N-(2-chloro-2-propenyl)-N-methoxycarbonylamino-acetonitrile) to a hogeneous phase. After the reaction was completed, the mixture was neutralzied with 8.4 g of 35% aqueous hydrochloric acid. The mixture was concentrated to dryness under reduced pressure. The residue was combined with acetonitrile and the mixture was stirred and filtered to remove inorganic salts. The filtrate was concentrated to dryness under reduced pressure. The residue was combined with 70 g of water and dissolved by elevating the temperature up to about 60° C. Then, the solution was gradually cooled to room temperature and precipitated crystals were collected by filtration and washed to give 4.78 g (purity: 90%, area percentage method) a pale yellow solid of 1-(2-chloro-2-propenyl)hydantoin.
Pure yield: 37% $^1$H-NMR (CDCl$_3$/TMS), (ppm): 3.96 (2H, s), 4.17 (2H, br. s), 5.44 (2H br. s), 9.2 (1H, br. s) mp, 117° to 119° C.

Example 4

Into a 100 ml four-neckecd flask were charged 5.9 g of water and 8.5 g (0.030 mole when purity was assumed to be 100%) of N-(4-bromrophenyl)methyl-N-methoxycarbonylamino-acetonitrile and they were heated in a water bath of 50° C. Then, 2.5 g (0.030 mole) of 48% aqueous sodium hydroxide solution was added dropwise thereto over 0.1 hour. Subsequently, the mixture was allowed to react in a water bath of 50° C. for 2 hours. As the reaction proceeded, the system changed from 2 phases (upper phase: water; lower phase: N-(4-bromophenyl)methyl-N-methoxycarbonylamino-acetonitrile) to a homogeneous phase. After the reaction was completed, the mixture was neutralized with 3.7 g of 35% aqueous hydrochloric acid at room temperature, during which crystals precipitated from the solution. The mixture was combined with 15.5 g of water and dissolved by elevating the temperature up to about 75° C. Then, the solution was gradually cooled to room temperature, precipitated pale yellow solid was collected by filtration and subjected to silica gel column chrormatography (ethyl acetate/hexane) to give 5.30 g of white solid of 1-[(4-bromophenyl)methyl]hydantoin which was virtually pure in $^1$H-NMR.

1H-NMR (CDCl3/TMS): (ppm): 3.79 (2H, s), 4.49 (2H, s), 7.15 (2H, d, J=8.0 Hz), 7.47 (2H, d, J=8.0 Hz), 9.2 (1H, br. s) mp: 150° to 154° C.

Example 5

Into a 500 ml four-necked flask was charged 20.2 g (0.505 mole) of sodium hydride (content: 60%) dispersed in oil. About 40 g of hexane was added under nitrogen stream and hexane was removed by decantation and the operation was repeated twice. Then, 139.4 g of tetrahydrofuran was added and, while cooling in a bath of ice-water, a solution of 52.2 g (0.457 mole) of N-methoxycarbonylamino-acetonitrile in 150.7 g of tetrahydrofuran was added dropwise over 1.5 hour. The mixture was brought to room temperature and allowed to react for 1 hour. Then, 59.7 g (0.502 mole) of 3-bromo-1-propyne was added dropwise at room temperature over 1.5 hour. After allowing the mixture to react at room temperature for 14 hours, 3.1 g (0.010 mole) of tetrabutyl ammonium bromide was added and the reaction was continued for additional 7 hour. After the reaction was completed, 98.2 g of water was added and phases were separated. The aqueous phase was extracted with ethyl acetate and the combined organic phases were treated with activated carbon and concentrated. The residue was subjected to silica gel column chromatogaphy (ethyl acetate/hexane) to give 65.9 g (purity: 98%; CC area percentage method) of an oil of N-(2-propynyl)-N-methoxycarbonylamino-acetonitrile.

Pure yield: 84% 1H-NMR (CDCl3/TMS): (ppm): 2.40 (1H, t, J=2.5 Hz), 3.74 (3H, s), 4.24 (2H, br. s), 4.35 (2H, br. s) Refractive index $n_D$: 1.4620 (27.5° C.)

Example 6

Into a 200 ml four-necked flask were charged 14.9 g (0.108 mole) of potassium carbonate 69.9 g of N,N-dimethylformamide and 11. 2 g (0.098 mole) of N-methoxycarbonylamino-acetonitrile and 12.8 g (0.108 mole) of 3-bromo-1-propyno was added dropwise at room temperature over 1.5 hour. The mixture was allowed to react at room temperature for 23 hours and 8 hours at 65° C. Then, 80.0 g of toluene and 280.0 g of water were added and phases were separated. The aqueous phase was extracted with toluene and the combined organic phases were treated with activated carbon, washed further with water and concentrated to give 5.7 g (purity: 75%; GC area percentage method) of an oil of N-(2-propynyl)-N-methoxycarbonylamino-acetonitrile.

Pure yield: 29%

Example 7

5 Into a 500 ml four-necked flask was charged 17.2 g (0.430 mole) of sodium hydride (content: 60%) dispersed in oil. About 30 g of hexane was added under nitrogen stream and hexane was removed by decantation and the operation was repeated twice. Then, 115.4 g of toluene was added and, while cooling in a bath of ice-water, a solution of 40.0 g (0.350 mole) of N-methoxycarbonylamino-acetonitrile in 115.4 g of tetrahydrofuran was added dropwise over 0.8 hour. The mixture was brought to room temperature and allowed to react for 4.8 hours. Then, 3.3 g (0.010 mole) of tetrabutyl ammonium bromide and subsequently a solution of 47.2 g (0.352 mole) of 2-propynyl methanesulfonate in 41.9 g of toluene were added dropwise at room temperature over 1.5 hour. The mixture was allowed to react at room temperature for 17 hours. After the reaction was completed, 100 ml of water was added and phases were separated. The aqueous phases were extracted with ethyl acetate and the combined organic phase was washed with water and concentrated. The residue was subjected to silica gel column chromatography (ethyl acetate/hexane) to give 50.0 g (purity: 89%; GC area percentage method) of an oil of N-(2-propynyl)-N-methoxycarbonylamino-acetonitrile.

Pure yield: 84%

Example 8

Into a 500 ml four-necked flask was charged 17.2 g (0.430 mole) of sodium hydride (content: 60%) dispersed in oil. About 30 g of hexane was added under nitrogen stream and hexane was removed by decantation and the operation was repeated twice. Then, 115.4 g of tetrahydrofuran was added and, while cooling in a bath of ice-water, a solution of 38.5 g (0.300 mole) of N-ethoxycarbonylamino-acetonitrile in 115.4 g of tetrahydrofuran was added dropwise over 1.8 hour. The mixture was brought to room temperature and allowed to react for 0.5 hour. Then, 57.1 g (0.480 mole) of 3-bromo-1-propyne was added dropwise at room temperature over 0.5 hour. After allowing the mixture to react at room temperature for 3.5 hours, 1.8 g (0.006 mole) of tetrabutyl ammonium bromide was added and the reaction was continued for additional 21 hours. After the reaction was completed, 100 ml of water was added and phases were separated. The aqueous phase was extracted with ethyl acetate and the combined organic phases were washed with water and concentrated. The residue was subjected to silica gel column chromatography (ethyl acetate/hexane) to give 41.3 g (purity: 90%; GC area percentage method) of an oil of N-(2-propynyl)-N-ethoxycarbonylamino-acetonitrile.

Pure yield: 75% 1H-NMR (CDCl3/TMS): δ (ppm): 1.28 (3H, t, J=7.1 Hz), 2.36 (1H, t, J=2.4 Hz), 4.21 (2H, q. J=7.1 Hz), 4.22 (2H, br. s), 4.32 (2H, br. s) Refractive index $n_D$: 1.4567 (27.5° C.)

Example 9

Into a 1,000 ml four-necked flask was charged 20.7 g (0.517 mole) of sodium bydride (content: 60%) dispersed in oil. About 60 g of hexane was added under nitrogen stream and hexane was removed by decantation and the operation was repeated twice. Then, 101.3 g of tetrahydrofuran was added and a solution of 55.2 g (0.484 mole) of N-methoxycarbonylamino-acetonitrile in 140.3 g of tetrahydrofuran was added dropwise at room temperature over 1.5 hour. After allowing the mixture to react for 1.8 hour, 3.9 g (0.012 mole) of tetrabutyl ammonium bromide and subsequently 70.5 g (0.635 mole) of 2,3-dichloro-1-propene were added dropwise at room temperature over 0.5 hour. After allowing the mixture to react at room temperature for 21.7 hours, excess sodium hydride was inactivated by the addition of 0.8 g of ethanol. Then, 200 ml of water and diethyl ether were added and phases were separated. The organic phases was washed with water, treated with activated carbon and concentrated to give 63.6 g (purity: 90%; GC area percentage method) of an oil of N-(2-chloro-2-propenyl)-N-methoxycarbonylamino-acetonitrile.

Pure yield: 62% 1H-NMR (CDCl3/TMS): δ (ppm): 3.79 (3H, s), 4.18 (2h, br. s), 4.26 (2H, br. s), 5.43 (2H, s) Refractive index $n_D$: 1.4761 (28.0° C.)

Example 10

Into a 200ml four-necked flask were charged 1.8 g (0.045 mole) of sodium hydride (content: 60%) dispersed in oil and 10.1 g of tetrahydrofuran, and two drops or ethanol were added thereto. Then, a solution of 5.0 g (0.044 mole) of N-methoxycarbonylamino-acetonitrile in 10.8 g of tetrahydrofuran was added dropwise over 1.7 hour. After allowing the mixture to react for 1.8 hour, a solution of 9.8 g (0.039 mole) of p-bromobenzyl bromide in 15.0 g of tetrahydrofuran was added at room temperature over 0.9 hour. After the reaction was continued for 43 hours, 20 ml of water and 40 ml of ethyl acetate were added and phases were separated. The aqueous phase was extracted with 40 ml of ethyl acetate and the combined organic phases were washed with water and concentrated. The residue treated with 10 ml of hexane, stirred Sufficiently and the hexane layer was removed. The residue was concentrated to give 10.8 g of an oil of N-(4-bromophenyl)methyl-N-methoxycarbonylamino-acetonitrile which was virtually pure in $^1$H-NMR.

$^1$H-NMR (CDCl$_3$/TMS): δ (ppm): 3.84 (3H, s), 4.11 (2H, br. s), 4.56 (2H, s), 7.15 (2H, d, J=8.0 Hz), 7.51 (2H, d, J=8.0 Hz) Refractive index n$_D$: 1.5451 (29.0° C.)

Production Examples for the N-alkoxycarbonylamino-acetonitrile derivatives of the Formula III wherein R$_1$ is methyl or ethyl are illustrated below. The purity of the product was obtained by gas chromatography (area percentage method) conducted under the following conditions and the pure yield was calculated by multiplying the crude yield by said purity.

Instrument: Shimadzu-GC-9A

Column: 1.6 m glass colunm, packed with XE-60

Inlet temperature: 250° C.

Column temperature: maintained at 100° C. for 3 minutes, raised to 200° C. at 5° C./min and maintained at the same temperature for 20 minutes:

Detector temperature: 250° C.

Carrier gas: N$_2$, at a flow rate of 60 ml/min

Detection: FID

Production Reference Example 1

Aminoacetonitrile sulfate (H$_2$NCH$_2$CN.1/2H$_2$SO$_4$, 121.5 g, 1.156mole) was dissolved in water (230.9 g) and the solution was cooled to 0° to 5° C. and adjusted to pH 5 to 7 by the addition of a small amount of 30% aqueous sodium hydroxide solution. Ethyl chloroformate (108.5 g, 1.00 mole) and 30% aqueous sodium hydroxide solution were concurrently added dropwise with stirring and keeping pH at 5 to 7 at 0° to 5° C. over 2 hours and the mixture was stirred at the same temperature for additional 2 hours while keeping the same pH by dropping, if necessary, 30% aqueous sodium hydroxide solution. The total amount of 30% aqueous sodium hydroxide solution was 294.3 g. The reaction mixture was extracted three times with toluene (485 ml). The toluene layer was dried over anhydrous magnesium sulfate, toluene was evaporated and the residue was cooled to room temperature to give crystals (124.7 g, 0.968 mole) of ethyl N-cyanomethylcarbamate.

Pure yield: 97%; Purity: 99.5% M.p.: 49.0° C. $^1$H-NMR (CDCl$_3$/TMS): δ (ppm): 5.60 (br. s, 1H), 4.15 (q, J=7.1 Hz, 2H), 4.12 (d, J=6.0 Hz, 2H), 1.25 (t, J=7.1, 3H)

Production Reference Example 2

Aminoacetonitrile sulfate (211.0 g, 2.01 moles) was dissolved in water (280.7 g) and 7.6 g of 48% aqueous sodium hydroxide solution was added at 10° to 20° C. to adjust pH at 4 to 5. Methyl chloroformate (198.9 g, 2.105 moles) and 48% aqueous sodium hydroxide solution were concurrently added dropwise with stirring and keeping pH at 4 to 5 at 10° to 25° C. over 8 hours and the mixture was stirred at the same temperature for additional 1 hour while keeping the same pH by dropping, if necessary, 48% aqueous sodium hydroxide solution. The amount of the used 48% aqueous sodium hydroxide solution was 346.6 g. The reaction mixture was extracted with a mixed solvent consisting of toluene (150 g) and ethyl acetate (150 g). Toluene and ethyl acetate were evaporated and the residue was cooled to room temperature to give crystals (210.4 g, 1.835 mole) of methyl N-cyanomethylcarbamte.

Pure yield: 91%; Purity: 99.5% M.p.: 49.0° C. $^1$H-NMR (CDCl$_3$/TMS): δ (ppm): 5.60 (br. s, 1H), 4.12 (d, J=6.0 Hz, 2H), 3.75 (s, 3H)

Production Reference Example 3

Aminoacetonitrile hydrochloride (84.0 g, 0.907 mole) was dissolved in water (98.2 g) and 12.0 g of 48% aqueous sodium hydroxide solution was added at 5° to 100° C. to adjust pH at 4 to 5. Methyl chloroformate (94.4 g, 1.00 mole) and 48t aqueous sodium hydroxide solution were concurrently added dropwise with stirring and keeping pH at 4 to 5 at 5° to 15° C. over 2 hours and the mixture was stirred at the same temperature for additional 1 hour while keeping the same pH by dropping, if necessary, 48% aqueous sodium hydroxide solution. The amount of the used 48% aqueous sodium hydroxide solution was 155.0 g. Ethyl acetate (200 ml) and water (30 ml) were added to the reaction mixture and crystals (NaCl) precipitated during the reaction were removed by filtration. The ethyl acetate layer was isolated and the aqueous layer was extracted twice with ethyl acetate (100 ml). Ethyl acetate was removed from the combined ethyl acetate layers and the residue was cooled to room temperature to give crystals (98.9 g, 0.835 mole) of methyl N-cyanomethylcarbamate. Pure yield: 95%; Purity: 99.5%

What is claimed:

1. A process for producing 1-substituted-hydantoin of Formula I:

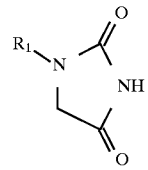

wherein R$_1$ represents a hydrocarbon group which may be substituted or a heterocyclic group which may be substituted which comprises the steps of;

(a) reacting N-substituted-N-alkoxycarbonylamino-acetonitrile of Formula II:

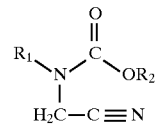

wherein R$_1$ is the same as defined above and
R$_2$ represents an alkyl group or a benzyl group which may be substituted, with a hydroxide selected from an alkali metal hydroxide and alkaline earth metal hydroxide and then (b) treating the resulting with an acid.

2. The process according to claim 1, in which the hydroxide is sodium hydroxide or potassium hydroxide.

3. The process according to claim 1 or 2, in which $R_1$ is an alkyl group, an alkenyl group, a halogenated alkenyl group, an alkynyl group, a benzyl group which may be substituted or a phenyl group which may be substituted.

4. The process according to claim 1, wherein $R_1$ represents a primary or secondary hydrocarbon group which may be substituted.

5. The process according to claim 4, which comprises reacting N-alkoxycarbonylamino-acetonitrile of Formula III:

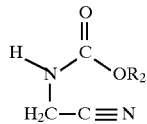

wherein $R_2$ represents an alkyl group or a benzyl group which may be substituted, with a compound of Formula IV:

wherein $R_1$ is the same as defined in claim 4 and x represents a halogen atom or a group of Formula:

$OSO_2Y$ wherein Y represents an alkyl group or a phenyl group which may be substituted, in the presence of a base to obtain N-substitued-N-alkoxycarbonylamino-acetonitrile of Formula II wherein $R_1$ and $R_2$ are as defined above, and further subjecting the N-substituted-N-alkoxycarbonylamino-acetonitrile to steps (a) and (b).

6. The process according to claim 4, in which the hydroxide is sodium hydroxide or potassium hydroxide.

7. The process according to claim 5 or 6, in which the base is sodium hydride.

8. A process for producing N-subtituted-N-alkoxycarbonylaminoacetonitrile of Formula III:

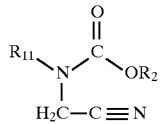

wherein $R_{11}$ represents a primary or secondary hydrocarbon group which may be sutbstituted and $R_2$ represents an alkyl group or a benzyl group which may be substituted, which comprises reacting N-alkoxycarbonylamino-acetonitrile of Formula III:

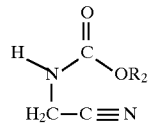

wherein $R_2$ represents the same as defined above, with a compound of Formula IV:

wherein $R_{11}$ is the same as defined above and X represents a halogen atom or a group of the Formula: $OSO_2Y$ wherein Y represents an alkyl group or a phenyl group which may be substituted.

9. The process according to claim 8, wherein the base is sodium hydride.

10. An N-alkynyl-N-alkoxycarbonylamino-acetonitrile compound of Formula V:

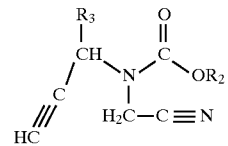

wherein $R_2$ represents an alkyl group or a benzyl group which may be substituted and $R_3$ represents a hydrogen atom or an alkyl group.

11. The N-alkynyl-N-alkoxycarbonylamino-acetonitrile compound according to claim 9, wherein $R_2$ represents an alkyl group or a benzyl group and $R_3$ represents a hydrogen atom.

* * * * *